(12) United States Patent
Mann

(10) Patent No.: US 6,877,388 B2
(45) Date of Patent: Apr. 12, 2005

(54) DEVICE FOR PREPARING A SAMPLE FOR ANALYSIS

(75) Inventor: Kari Mann, Espoo (FI)

(73) Assignee: Outokumpu Oyj, Espoo (FI)

( * ) Notice: Subject to any disclaimer, the term of this patent is extended or adjusted under 35 U.S.C. 154(b) by 0 days.

(21) Appl. No.: 10/399,885

(22) PCT Filed: Oct. 23, 2001

(86) PCT No.: PCT/FI01/00914
§ 371 (c)(1),
(2), (4) Date: Apr. 22, 2003

(87) PCT Pub. No.: WO02/34651
PCT Pub. Date: May 2, 2002

(65) Prior Publication Data
US 2004/0011148 A1 Jan. 22, 2004

(30) Foreign Application Priority Data
Oct. 26, 2000 (FI) .............................................. 20002350

(51) Int. Cl.$^7$ ................................................. G01N 1/10
(52) U.S. Cl. .................................. 73/863.51; 73/864.81
(58) Field of Search ...................... 73/863.51, 863.52, 73/864.81, 864.83, 865.18

(56) References Cited

U.S. PATENT DOCUMENTS

| 3,092,882 A | * | 6/1963 | Dietert ........................ 366/17 |
| 4,074,138 A | | 2/1978 | Bosshard ..................... 250/435 |
| 4,105,558 A | * | 8/1978 | Heinrich et al. ............. 210/199 |
| 4,718,288 A | * | 1/1988 | Leschonski et al. .......... 73/863 |
| 4,976,540 A | | 12/1990 | Kitamura et al. ............. 356/38 |
| 5,074,158 A | | 12/1991 | Tokoyama ................. 73/865.8 |
| 6,391,236 B1 | * | 5/2002 | Franceschini ............... 264/112 |

FOREIGN PATENT DOCUMENTS

| DE | 25 25 261 | 12/1976 | ............ G01N/1/28 |
| JP | 59-154132 | 9/1984 | ............. B01J/4/00 |

* cited by examiner

Primary Examiner—Charles Garber
(74) Attorney, Agent, or Firm—Morgan & Finnegan, LLP

(57) ABSTRACT

The invention relates to a device for preparing a sample meant for continuously operated on-line analysis and containing finely divided, pulverous material, so that the sample is suited for an analysing method designed to analysing the surface layer of the sample, and that a sample flow extracted from the material flow by a sampler is conducted to the device. According to the invention, in order to realize an essentially even sample material bed (10) to be transported past the analyser device (11), the height of the sample material in the sample material bed feeder element (5) is maintained essentially at a predetermined value.

12 Claims, 3 Drawing Sheets

DEVICE FOR PREPARING A SAMPLE FOR ANALYSIS

Figure 1:
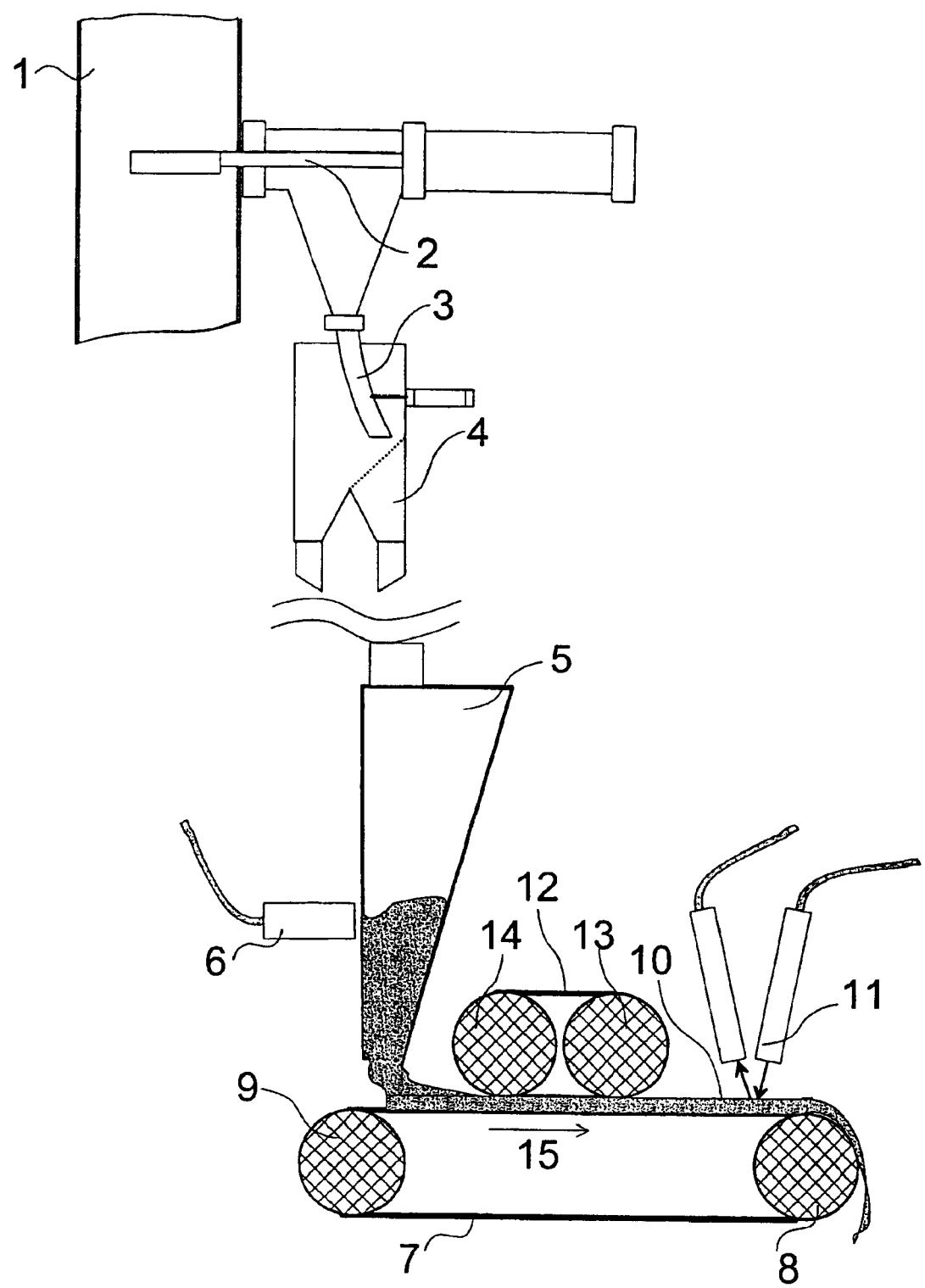

The present invention relates to a device for preparing a sample containing finely divided, pulverous material meant for continuously operated on-line analysis, to be suitable for an analysing method directed to the surface layer of the sample.

In order to analyse a finely divided, pulverous sample, the sample is often compressed into a briquette for analysis. The obtained briquette is further brought into an analyser. However, it is apparent that the process of producing a briquette for analysing a sample is complicated and sensitive to disturbances, when a finely divided, pulverous sample should be analysed in a continuously operated on-line analysis. For the on-line analysis, the finely divided, pulverous sample is usually conducted to a measuring cell in a flowing form. Through a window attached to the measuring cell wall, the sample passing by the window is analysed by applying for example X-ray fluorescence as the measuring method. Measuring cells designed for continuously operated on-line analysis are described for instance in the U.S. Pat. Nos. 5,048,325 and 5,212,994.

In the U.S. Pat. No. 5,048,325, the sample flow is directed at an inclined position towards a measuring window attached to the measuring cell wall, so that the sample flow is directed near the inner surface of the measuring window. Now the sample flow glides at an essentially even pace by the measuring window. In the U.S. Pat. No. 5,212,994, inside the measuring cell, in the vicinity of the measuring window attached to the measuring cell wall, there is installed a feeder that divides the sample flow into sub-flows, so that an essentially continuous sample flow passes by the measuring window.

In the above described systems for conducting a sample flow to on-line analysis, the sample flow is measured through a measuring window attached to the measuring cell wall. A measurement carried out through a measuring window essentially weakens the performance of the employed measuring method, if the measuring signal is attenuated in the window material. Moreover, a fixed measuring window often makes the material layer that is located immediately next to the measuring window unrepresentative. In order to ensure a good performance, the measuring equipment of the measuring method must therefore be designed to be sufficiently strong, which as such increases both the expenses and the hazards possibly caused by the measuring method.

The height of the top surface of the material bed passing by an analyser is in the WO patent application 99/45368 measured with laser beams, when the top surface of the material bed remains within predetermined limits. This is achieved by focusing the laser beams on the surface to be measured. If the measured surface is not located in the focusing area, the measurement is not carried out. Thus the WO patent application 99/45368 is best suited for observing the height of the measured surface, and for giving an alarm of a possible change in the surface height.

The object of the present invention is to eliminate some of the drawbacks of the prior art and to achieve an improved device for preparing a sample containing finely divided, pulverous material for on-line analysis, so that the sample prepared in said device is made to pass by the measuring device in an essentially even flow, without having to analyse the sample through a separate measuring window. The essential novel features of the invention are apparent from the appended claims.

According to the invention, a sample extracted from a process flow containing finely divided, pulverous material, is by means of a partition element conducted as a flow either to a feeder element, with a degree of fullness that is kept essentially constant, or as a bypass flow back to the material flow containing finely divided, pulverous material. The feeder element is installed in a position where the sample containing finely divided, pulverous material is discharged from the feeder element to the conveyor element in an essentially even fashion, so that the sample is made to form an essentially even sample material bed onto the conveyor element that is arranged in an essentially horizontal position. By means of the conveyor element, the sample material bed is transported past the analyser device, which analyses the surface layer of the sample material bed. Owing to the even sample material bed, the distance between the sample material bed and the analyser device can be maintained essentially constant, so that also the measuring signal obtained from the analyser device is maintained fit for comparison during the whole measuring process. After analysing, the sample material flow is returned to the process flow containing finely divided, pulverous material. When necessary, part of the analysed sample material flow is recovered for a calibration sample.

To the device according to the invention, the sample flow can also be extracted from a finely divided pulverous material that is at least partly elutriated. The elutriated material is subjected to drying, advantageously while the material is placed on the conveyor element, prior to the analysis proper. In connection with the drying process, the material is heated both by means of heating elements connected to the conveyor belt and, when necessary, also by means of heating elements placed outside the conveyor belt in order to remove the moisture contained in the material.

Advantageously the feeder element of the device according to the invention is a feed funnel, a vibration feeder or a feeder element provided with a vibrator. The feeder element is further provided with a measuring element, such as a level detector, which measures the level of the sample to be fed in the feeder element and containing finely divided, pulverous material. When the level reaches a predetermined value, the sample material flow into the feeder element is interrupted, and the sample flow coming from the sampler is conducted back to the main material flow. The level detector can also be connected directly to the sampler placed in the main material flow, in which case the sampler interrupts the sampling from the main material flow.

In the device according to the invention, the sample flow to be analysed and containing finely divided, pulverous material is discharged from the feeder element onto an essentially continuously operated conveyor element, such as a belt conveyor, as an essentially even sample material bed owing to the essentially even sample material quantity contained in the feeder element. The conveyor element transports the sample material bed further towards the point of measurement, where the sample material bed is subjected to analysis.

In order to make the process of analysing the sample material bed more effective by means of device according to the invention, a smoothing element can be installed above the sample material bed, which smoothing element smoothes out the surface layer of the sample material bed to be suitable for analysis. Advantageously the smoothing element is for instance a belt conveyor, which is shorter than the conveyor element proper and is installed so that the conveyor belt, in the part underneath the drawing drum and the folding drum, forms a contact with the surface layer placed on the conveyor belt of the transporting conveyor element. The conveyor belt surface formed by the smoothing element may also be provided with smoothing elements that are installed in order to create a contact, instead of the conveyor belt, with the surface layer placed on the conveyor belt of the conveyor element transporting the sample material bed. Moreover, the smoothing element can be for example a drum that is installed in order to create a contact with the surface layer placed on the conveyor belt of the conveyor element transporting the sample material bed, or the drum surface can be provided with smoothing elements in order to create a contact point with the surface layer placed on the conveyor belt of the conveyor element transporting the sample material bed. The employed smoothing element can likewise be for example a fixed smoother installed in a transversal or inclined position with respect to the proceeding direction of the sample material bed, which is installed in order to create a contact with the surface layer with respect to the conveyor belt of the conveyor element transporting the sample material bed.

The sample material bed extracted by means of the device according to the invention from a process flow containing finely divided, pulverous material is advantageously made to flow underneath the analyser device as an even sample material bed, so that the material placed on the surface of the sample material bed essentially represents the contents and grain size classes of the whole sample material bed. At the same time the height of the sample material bed is maintained essentially at a standard height, in which case also the mutual distance between the material surface to be analysed and the analyser device is maintained essentially constant during the whole measuring operation.

The device according to the invention for preparing samples containing finely divided, pulverous material is suited to be used in connection with various measuring methods. The use of the device according to the invention is particularly advantageous when the measuring information that forms the basis for the analysis is obtained from the surface layer of the sample material, or when the measuring signal is dependent on the distance between the measuring device and the sample. Among such measuring methods, let us point out for instance the LIBS (Laser Induced Breakdown Spectroscopy), X-ray fluorescence, optical image analysis and moisture analysis based on infrared absorption.

Figure 2:
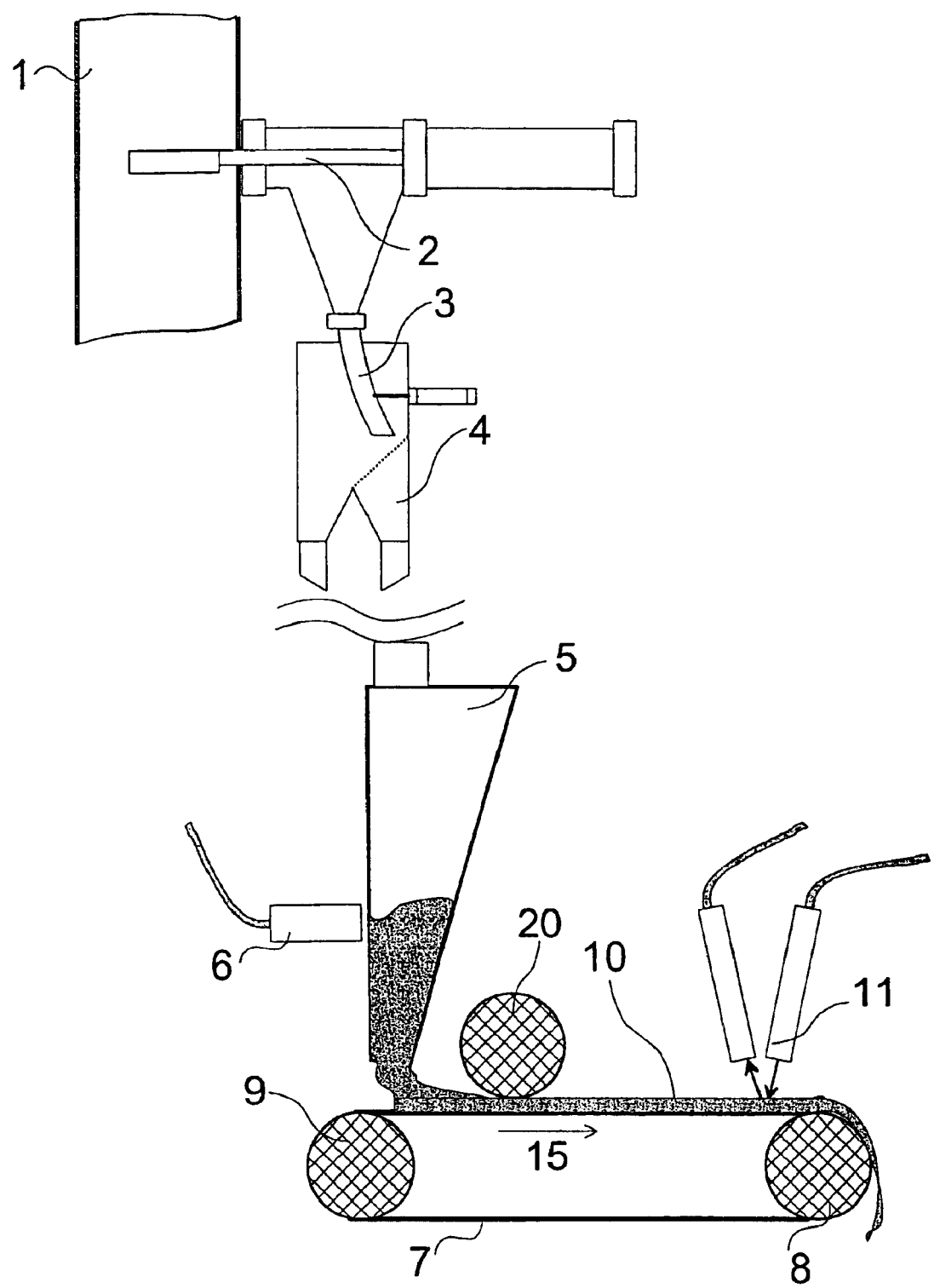
Figure 3:
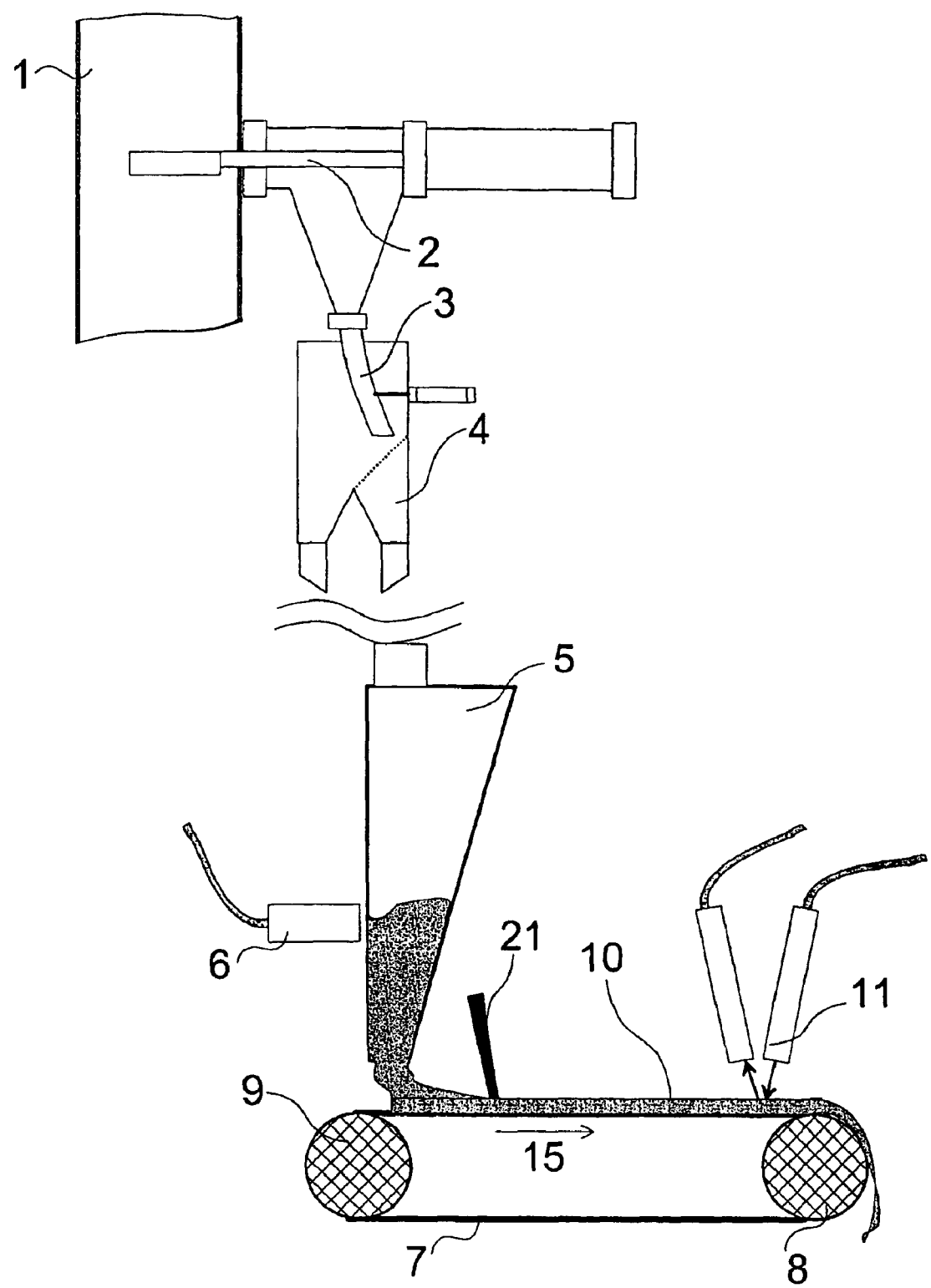

The invention is explained in more detail below, with reference to the appended drawings, where FIG. 1 shows a preferred embodiment of the invention, seen in a schematical side-view illustration, FIG. 2 shows another preferred embodiment of the invention, seen in a schematical side-view illustration, and FIG. 3 shows a third preferred embodiment of the invention, seen in a schematical side-view illustration.

According to FIG. 1, the finely divided, pulverous material flows in a pipe 1, inside which there is partially installed a sampler 2. The sampler 2 is advantageously made to operate in an essentially continuously operation in order to achieve a continuous sample material flow. From the sampler 2, the sample material flow is conducted to the sample partition element 3 that guides the sample material flow either to the channel 4 leading to the feeder element 5 of the material bed formed of the sample material flow or back to the original finely divided, pulverous material flow in the pipe 1. The sample material is allowed to flow into the feeder element 5 as long as the sample material flow reaches in the feeder element 5 a level that is higher than the predetermined value. The height of the sample material flow level is measured by a level detector 6 connected to the feeder element 5, which detector, after said level is surpassed, sends a command for the partition element 3 to interrupt the sample material flow entering the feeder element 5 and to conduct the sample material flow back into the pipe 1. The level detector 6 may also send the command directly to the sampler 2 in order to interrupt the reception of the sample material flow from the pipe 1.

From the bottom part of the feed funnel serving as the feeder element 5, the sample material flow is discharged to underneath the feeder element 5, onto a belt conveyor 7 placed in an essentially horizontal position, which belt conveyor is made to rotate between the drawing drum 8 and the folding drum 9. Owing to the even surface height maintained by means of the detector 6 connected to the feeder element 5, the sample material flow forms on the belt conveyor 7 an essentially even sample material bed 10. By means of the belt conveyor 7, the sample material bed 10 is transported towards the analyser device 11. In order to maintain the height of the sample material bed 10 placed on the belt conveyor 7 at essentially the predetermined value, and simultaneously in order to make constant the distance between the analyser device 11 and the surface layer of the sample material bed 10 placed on the belt conveyor 7, between the feeder element 5 and the analyser device 11, above the conveyor belt 7, there is installed a second belt conveyor 12 serving as the smoothing element. The conveyor belt 12 serving as the smoothing element is made to rotate between the drawing drum 13 and the folding drum 14, so that the conveyor belt of the belt conveyor 12 serving as the smoothing element passes, on the part located underneath drawing drum 13 and the folding drum 14, in parallel with the proceeding direction 15 of the sample material bed 10. The belt conveyor 12 serving as the smoothing element is installed, in relation to the belt conveyor 7 transporting the sample material bed 10, so that the belt conveyor 12 serving as the smoothing element creates a contact with the surface layer of the sample material bed 10 placed on the belt conveyor 7 while passing in the proceeding direction 15 of the sample material bed 10. Thus the belt conveyor 12 serving as the smoothing element results in a smoothing of the surface layer of the sample material bed 10 placed on the belt conveyor 7.

After the belt conveyor 12 serving as the smoothing element, the sample material bed 10 is transported past the analyser device 11, which analyser device 11, using the LIBS analysing technique, analyses the sample material bed 10 on the basis of the material contained in the surface layer of the sample material bed 10 placed on the belt conveyor 7.

In FIG. 2, the belt conveyor 12 serving as the smoothing element is replaced by a smoothing drum 20, which drum, while rotating above the belt conveyor 7 is in contact with the surface layer placed on the belt conveyor 7 and thus smoothes out the surface layer to be advantageous for the analysing process carried out by the analyser device 11.

In FIG. 3, the smoothing element 21 of the sample material bed 10 is a fixed smoothing element installed so that the smoothing element 21 creates a contact with the surface layer placed on the belt conveyor 7 in order to advantageously smooth out the surface layer for the analysing process carried out by the analyser device 11.

What is claimed is:

1. A device for preparing a sample for continuous on-line analysis of finely divided, pulverized material, said device comprising:

a sampler for diverting sample material of the finely divided, pulverized material from a material flow;

a feeder element for discharging sample material in an essentially even fashion onto a conveyer element forming an essentially even bed of sample material on the conveyer element;

the conveyer element for transporting the essentially even bed of sample material from the feeder element to an analyser;

an analyser to analyse a surface layer of the bed of sample material;

a smoothing element for contacting and smoothing out the surface layer of the essentially even sample material bed so that an essentially even sample material bed with a surface layer that has been smoothed out is transported past the analyzer;

a measuring element for measuring the height of the sample material contained in said feeder element; and the partition element and the measuring element being interconnected to allow sample material to be sent to the feeder element if a level of material in the feeder element detected by the measuring element is below a predetermined value; and to further allow the sample material to be diverted back to a material flow if a level of material in the feeder element detected by the measuring element is above a predetermined value.

2. A device according to claim 1, further comprising a movable partition element for diverting a desired amount of material to the feeder element, said partition element being located in a sample material flow path, the sample material being diverted by the partition element prior to reaching the feeder element.

3. A device according to claim 1 wherein the sampler and the measuring element are interconnected to allow a sampler to obtain a portion the sample material from the material flow, to be sent to the feeder element, if a level of material in the feeder element detected by the measuring element is below a predetermined value; and to further allow interruption of sampling by the sampler if the level of sample material in the feeder element is above a predetermined value.

4. A device according to claim 1, wherein the conveyor element that transports the sample material bed from the feeder element to the analyser device is a belt conveyor.

5. A device according to claim 1, wherein the smoothing element is a smoothing drum.

6. A device according to claim 1, wherein the smoothing element is a fixed smoother.

7. A device according to claim 6, wherein said fixed smoother is substantially planar.

8. A device according to claim 1, further comprising smoothing parts on the surface of the smoothing element.

9. A device according to claim 1, wherein the conveyor element is in an essentially horizontal position.

10. A device according to claim 1, wherein the conveyor element is a conveyor belt.

11. A device for preparing a sample for continuous on-line analysis of finely divided, pulverized material, said device comprising:

a sampler for diverting sample material of the finely divided, pulverized material from a material flow;

a feeder element for discharging sample material in an essentially even fashion onto a conveyer element forming an essentially even bed of sample material on the conveyor element;

the conveyer element for transporting the essentially even bed of sample material from the feeder element to an analyser;

an analyser to analyse a surface layer of the bed of sample material;

a smoothing element for contacting and smoothing out the surface layer of the essentially even sample material bed so that an essentially even sample material bed with a surface layer that has been smoothed out is transported past the analyzer; and wherein the smoothing element is a belt conveyor.

12. A device for preparing a sample for continuous on-line analysis of finely divided, pulverized material, said device comprising:

a sampler for diverting sample material of the finely divided, pulverized material from a material flow;

a feeder element for discharging sample material in an essentially even fashion onto a conveyer element forming an essentially even bed of sample material on the conveyor element;

the conveyer element for transporting the essentially even bed of sample material from the feeder element to an analyser;

an analyser to analyse a surface layer of the bed of sample material;

a smoothing element for contacting and smoothing out the surface layer of the essentially even sample material bed so that an essentially even sample material bed with a surface layer that has been smoothed out is transported past the analyzer; and wherein the conveyor element is provided with heating elements in order to dry the material to be analysed.

* * * * *